(12) United States Patent
Moreno (10) Patent No.: US 7,701,353 B1
(45) Date of Patent: Apr. 20, 2010

(54) INDIVIDUAL SYSTEM PERFORMANCE MANAGEMENT

(76) Inventor: Carlos W. Moreno, 35 Oliver Rd., Cincinnati, OH (US) 45215

( * ) Notice: Subject to any disclaimer, the term of this patent is extended or adjusted under 35 U.S.C. 154(b) by 0 days.

(21) Appl. No.: 11/618,133

(22) Filed: Dec. 29, 2006

Related U.S. Application Data (60) Provisional application No. 60/755,534, filed on Dec. 30, 2005.

(51) Int. Cl.
*G08B 23/00* (2006.01)

(52) U.S. Cl. .............................. 340/573.3; 340/539.12; 340/573.1; 706/11; 706/45; 706/924

(58) Field of Classification Search ............ 340/539.12, 340/573.1; 706/11, 45
See application file for complete search history.

(56) References Cited

U.S. PATENT DOCUMENTS 4,872,122 A * 10/1989 Altschuler et al. ............ 706/12
6,687,685 B1 * 2/2004 Sadeghi et al. ................ 706/15
7,433,853 B2 * 10/2008 Brockway et al. ............. 706/45

OTHER PUBLICATIONS

Moreno, C.W. (2001) "Comparison of two well known Methods for Optimizing Power Plant Operations", 44th Annual ISA Power Industry Div. Conference, Orlando, Florida, USA Jul. 7-13, 2001.*
Adelman, A., "Process Improvement by the Complex Method," AICHE Journal, vol. 18(1) (Jan. 1972) pp. 20-24.
Box, M.J., A New Method of Constrained Optimization and a Comparison with Other Methods, Computer Journal, vol. 6 (1965) pp. 42-52.
Box, GEP, Empirical Model Building and Response Surfaces, John Wiley & Sons, New York (1987).
Box, GEP, Evolutionary Operations, John Wiley & Sons, New York (1969).
Colosimo, B.M. et al., "An Application of Bayesian Statistics to Sequential Empirical Optimization," Chap. 11, p. 291, Bayesian Process Montioring, Control and Optimization, Chapman & Hall, Bacon Raton, Fl (2007).
Dharmarajan, N. et al., "Boiler Tuning with SPO: The Critical First Step in the NOx Compliance Strategy of Central & South West Company," AWMA Conference and Expo, Nashville, TN (Jun. 1996) pp. 1-11.
Draper, N., Applied Regression Analysis, John Wiley & Sons, New York (1996).
Hurwitz, A., "Sequential Process Optimization with a Commercial Package," 6th National Symposium: Statistics and Design in Automated Manufacturing (Feb. 1993) pp. 1-19.

(Continued)

*Primary Examiner*—Benjamin C Lee
*Assistant Examiner*—Samuel J Walk
(74) *Attorney, Agent, or Firm*—Frost Brown Todd LLC (57) ABSTRACT

Individual System Performance Management apparatus employs in one manifestation Sequential Empirical Optimization (SEO) in its illustrative version to manage a sequence of periodic readjustment to adjust inputs of an input/output system with the aim to maximize the cumulative sequence of overall value delivered by the system. SEO continually updates its learning from the stored run data. In this discussion, the term "adjusting" control inputs is used the same as "setting" control inputs, including adjusting or setting things by hand.

11 Claims, 4 Drawing Sheets

OTHER PUBLICATIONS

McVay, M. et al., "Illinois Power's Online Dynamic Optimization of Cyclone Boilers for Efficiency and Emissions Improvement," International Joint Power Generation Conference, Baltimore, MD (Aug. 24, 1998) pp. 1-12.

Moreno, C., "Comparison of two well known Methods for Optimizing Power Plant Operations," $44^{th}$ Annual ISA Power Industry Division Conference, Orlando, FL (Jul. 7-13, 2001) pp. 1-8.

Moreno, C., "Gaining Control of Plastics Forming Machines with New Technology for On-Line Adjustments," 1994 Structural Plastics Conference, Washington D.C. (Apr. 10-13, 1994) pp. 1-15.

Moreno, C., "How Modern 'Smarter Not Harder' Technologies May *Simultaneously* Maximize the Combination of Pollution Reduction and Business Success," Conference on Environmental Commerce, CONEC'93, Chattanooga, TN (Oct. 17-20, 1993) pp. 1-11.

Moreno, C., "Improvements Through Process Adjustments," ASA 1999 Quality and Productivity Research Conference, Schenectady, NY (May 19-21, 1999) pp. 1-14.

Moreno, C., "Software: a gentler step-up: the technology reproduces the process of a person learning how to perform a task better," *http://www.isa.org/PrinterTemplate.cfm?Section=InTech*__Home1&template=/ContentMan (Apr. 1, 2006) pp. 1-2.

Moreno, C. et al., "Reducing NOx Emissions and Improving Boiler Efficiency Using Synthetic Intelligence," Expert System Applications for the Electric Power Industry, EPRI Expert Systems (Dec. 8-10, 1993) Phoenix, AZ, pp. 1-17.

Nachtsheim, C.J., "Tools for Computer-Aided Design of Experiments," Journal of Quality Technology, vol. 19(3) (Jul. 1987) pp. 132-160.

Sachs, E.M., "Process Control System for VLS Fabrication," IEEE Transactions on Semiconductor Manufacturing, vol. 4(2) (May 1991) pp. 134-144.

Spendley, W., "Sequential Applications of Simplex Designs in Optimization and EVOP," Technometrics, vol. 4(4) (Nov. 1962) pp. 441-461.

* cited by examiner

INDIVIDUAL SYSTEM PERFORMANCE MANAGEMENT

CROSS REFERENCE TO RELATED APPLICATIONS

The present application hereby claims the benefit of the provisional patent application of the same title, Ser. No. 60/755,534, filed on 30 Dec. 2005, the disclosure of which is hereby incorporated by reference in its entirety.

FIELD OF THE INVENTION

The present invention relates, in general, to devices to optimize operating performance of existing systems, by managing better and dynamically the adjustable decision inputs, and in one embodiment learning and refining how to do so by the continual collection of operating data.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

The Individual System Performance Management (ISPM) advises decisions to manage the operations of an individual input/output (I/O) system to improve its operating performance. Depending on the uses and circumstances the decisions may be implemented automatically. ISPM is a device with multi-input, multi-output logic that uses data and mathematics to learn and aid the user in how to achieve better overall performance with an existing system.

Desirability of performance for each individual I/O system may be defined by the user or expert by: (a) any input/output value satisfying high and/or low constraints (typically capacity and safety considerations), and/or (b) when the constraints are satisfied, by the value of a Performance Index to be maximized or minimized. The Performance Index may be calculated as a function of inputs and output values—and coefficients (e.g., fuel unit cost) may be updated by the user. The Performance Index may be an economic evaluation or any measure of operating "performance", "goodness", "satisfaction" or "desirability".

Operations of an individual I/O system creates output (response) values which depend on the values of the inputs. The ISPM is useful when there are various possible levels of operating performance or its desirability—which means that there are sufficiently large possible combinations of input values.

The inputs range from the inevitable (e.g., outside air temperature, purity of an ingredient), through those which are difficult to choose or adjust (e.g., gear ratios), to those inputs that are easy to adjust (e.g., flow settings).

Figure 1:
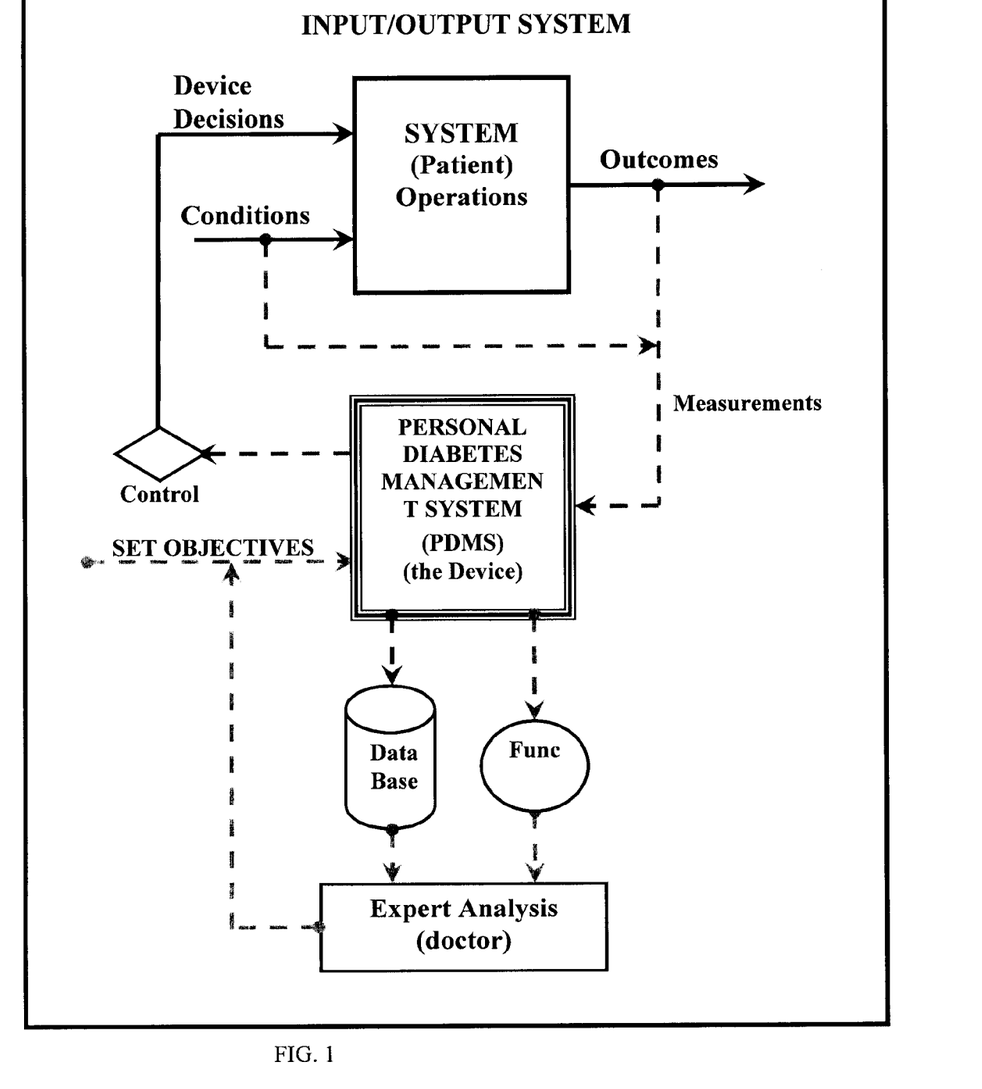
FIG. 1 is a block diagram of an Individual System Performance Management apparatus.

Even though there is not a distinct dichotomy, and in order to be able to use current mathematical tools, it is useful at any one time to think about two types of inputs (see FIG. 1 below):

(1) Conditions—that determine the corresponding optimal Device Decision values;
 (a) the Inevitable inputs which are practically impossible to change;
 (b) the decisions which are already set in place or the user is about to implement; and
 (c) for system with memory, recent past inputs and outputs (done automatically).

(2) Device Decisions for which the user wants the ISPM to suggest near-optimal values. This includes modifications to the advice given by built-in control rules to get better operating performance. Which decisions belong to the set of Device Decisions is determined at the time of requesting ISPM for an advice.

One objective of the ISPM is to enable making a sequence of Device Decisions that would make operations the most desirable possible, given the possibly changing known Conditions. That is, an objective of ISPM is optimization—sometimes referred to as "conditional optimization".

One application is when a very accurate mathematical function of the system's performance do not exist. Another application is when the system is not a production process. Yet another application is when the system is an individual living being. Yet another application is when the living being is a human body. Yet another application is when the living being is the user's personal body. Yet another application is when the human body has a disease. Yet another application is when the disease is chronic. Yet another application is when the disease is diabetes.

As applied to the management of diabetes this product may be called Personal Diabetes Management System (PDMS). One possible example of a PDMS application at any one time would be:

(1) Conditions
 (a) Inevitable situations that the body has to live with, such as temperature, forced activities, forced ingestions, medicament availability, etc.;
 (b) Decisions that the user wishes to make for whatever reasons, such as going for a walk, eating a large steak, drinking three glasses of wine with dinner, eating apple pie, etc.
(2) Device Decisions
 (a) Time and amount of medications. These might include insulin complements, enhancing insulin production, reducing insulin resistance, slowing absorption of carbohydrates.
 (b) Time and amount of each food/drink group—e.g., consumption of carbohydrates.
 (c) Time and amount of each activity.
(3) Outputs (Consequences or Results of inputs)
 (a) Outputs related to diabetes such as amount of sugar in the blood, lipids;
 (b) Performance Index; e.g. how close to target values the blood sugar is, plus the "burden" or side effects of the medicaments taken.

The PDMS serves the patient as frequently as desired so that, given Conditions, it advises the best remaining decisions and predicts the corresponding expected outputs. Alternatively, the user may suggest a complete set of input values and the PDMS would display expected outputs (What-If function).

Some benefits for the user are: awareness of results and lower probability and gravity of hyperglycemia and hypoglycemia, and in general, more flexibility and higher quality of life, what is called "wellbeing".

The PDMS may be embodied as software to be used in a personal computer. In other embodiments, it may reside in a hand-held device such as a Personal Digital Assistant (PDA) or be in a specially designed device. In still other embodiments, there will also be sensors such as glucose meters to collect data automatically, and even automatic dispensers such as an ambulatory insulin pump. Communications with sensor or delivery devices in or on the surface of the body may be wireless. Equivalently for other deceases, and for other activities and systems, including skippering a sail boat, guiding a robot, or the operations of a fuel-injection system.

ISPM Setup. Setup comprises defining the inputs, outputs; and setting the objectives as defined by Constraints and the Performance Index—all of which depend on the system or situation to be managed. Setup may be fixed during device production, or part or all be flexible to be re-defined by the user. In the case of PDMS, many variables may be mandated by a physician.

ISPM Operations. After the ISPM is seeded with sufficient individual system input/output data to be useful (explained below) its regular use will include two activities:

(1) Data Entry: The user will enter, at some frequency to be determined, the new conditions experienced, the new decisions made (either independently or with ISPM's advice), and results (outputs) experienced. In more advanced options some or all data may be collected automatically.

(2) Advice: When desired, given the Conditions, the user will question the ISPM for advice on what to do with the remaining decisions (including all) to maximize performance. The user may or may not follow the advice, but whatever he/she does, that will be actual data to be entered. In more advanced designs there may be options where some or all advice may be implemented automatically. The ISPM would also display the expected outputs from following the Advice, and the level of uncertainty. It may also advise whether no action may produce satisfactory results (e.g., sufficient well-being); which may be interpreted as that the Decisions in the Conditions are not sufficiently wise given the objectives to be achieved.

Seeding involves Data Entry of input/outputs for the individual system, for a period of time to be determined, for instance, one month. After that period, the advice will be judged according to experience and common sense (e.g., medical criteria for PDMS) until it is deemed sufficiently reliable.

TECHNOLOGY. The basic assumption made is that each individual system has a stable input/output system for a particular mode of operations. That is, the ISPM is applicable when the I/O system has a fairly constant "transfer function" that creates outputs as a function of the inputs. If the transfer function changes, something else is the matter, and probably an expert needs to look at what is going on. Ignoring an important input that keeps on changing would appear as a transfer function that changes. Thus, this device would work best when all important inputs are known and their values included in the setup. For systems that have "memory", the outputs may also be a function of past conditions and decisions.

A key concept in the Claim is that a sufficiently accurate transfer function based on prior knowledge and data exists, and/or that it "learns" an approximate one by fitting a mathematical function to the data. To do the fitting, one uses some of a variety of standard or especially developed mathematical/statistical functions and/or computer programs. Then in addition, standard or especially developed optimization search engines to identify near-optimal conditional decisions as estimated by those approximate functions based on the conditions are needed. Examples are (in approximate order of age): (1) Linear Regression and Linear Programming (Optimization); (2) Non-linear Regression and Non-linear Programming (Optimization); (3) Sequential Empirical Optimization (SEO); (4) Neural Networks (NN) and optimization; and (5) others more specialized for this application. Any of these technologies may be customized and expanded so as to: (1) Update the fitted models periodically with new stored data, to refine its knowledge and keep up with changes in the systems behavior. (2) Add built-in control rules so that, depending on conditions, some preliminary decisions are recommended based on prior general knowledge for a family of individual systems. The Device Decisions include modifications of the advice by the preliminary control rules to best suit the individual system. In the case of PDMS, the "control rules" would be the current, static treatment recommendations. The control rules may be updated with refined new knowledge and (3) Add a generic transfer function based on prior general knowledge for a family of individual systems, so that an advice without any data would be a generic advice, not individualized. Then the fitting mathematics may create a correction transfer function which, together with the generic transfer function, will characterize the individual system's behavior. The generic transfer function may be updated with refined new knowledge.

Some features of the ISPM solution: (1) learns how the I/O individual system behaves based on the history of data, even as the transfer function changes slowly with time, such a due to seasons, wear-and-tear, age, etc. (2) may detect whether there is a sudden change in behavior due to unknown causes, to trigger an alert to pay more attention or to bring to bear expert advice and possibly take corrective action outside the ISPM. (3) may detect whether past data seems to be incongruous or erroneous. (4) may detect the relative importance of the inputs as based on the data. (5) may be download to a computer for analysis by experts and management of past data and the setup.

The diagram of FIG. 1 is labeled as for the PDMS application. The dotted lines indicate flow of data. The green dotted lines indicates frequent exchange of data. The orange dotted lines are less frequent interactions by which the user or experts guide the ISPM, or in this case the PDMS.

The "Data Base" and the "Functions" (including the transfer functions and/or the built-in control rules) are really within the Device. The expert (e.g., a specialized physician in a PDMS) will review past data and the characteristics of the (approximate) transfer function to draw insights about the particular aspects of this input/output system (the patient) and the conditions under which it is subjected. This analysis may result in resetting the specifics of the application (variables, objectives, rules, etc.).

A desirable manifestation of the optimization technology is Sequential Empirical Optimization (SEO) already used as computer software for optimizing production/manufacturing operating performance, but not including all the features described in this patent. SEO exists today in only one commercial product ULTRAMAX®. The SEO Technology—Introduction. Basically SEO manages a sequence of periodic readjustment to the control inputs of an input/output system with the aim to maximize the cumulative sequence of overall value delivered by the process. SEO continually updates its learning from the stored run data. In this discussion, the term "adjusting" control inputs is used the same as "setting" control inputs, including adjusting or setting things by hand. (SEO might not, but the idea of this Device may include this logic).

Some earlier approaches to solve this problem were EVOP (e.g., Box and Draper, 1969) and SIMPLEX (Spendley, Hext and Himsworth; 1962, Walters, F. H. et al. 1991). As computer power became accessible to production in the late 60's, Dr. Moreno lead efforts within Procter & Gamble to develop and implement new algorithms taking advantage of what is possible with computer programming and advanced statistical modeling in order to vastly overcome the limitations of those earlier methods.

The SEO started in 1982 is the third version started from scratch. Several hundreds of individual processes have been optimized with ULTRAMAX.

Desirable SEO features: These are the properties which are necessary, or highly desirable, for managing process adjustments, and define SEO (from Moreno, 1993, 1994): (1) User Control: As one aspect of flexibility, users are not required to follow the sequential advice provided by the technology. This is desirable for early acceptance. It is also desirable during the earlier adjustment cycles when very little data has been collected, to enable existing experience to be included in the run data base.

(2) Sequential cycles may be stopped at any time to allow you to continue taking advantage of the gains achieved so far. Later on, you may continue where you left off, making use of the stored run data.

(3) Multiple inputs, multiple outputs: It deals with multiple inputs (some adjusted, some uncontrolled) affecting multiple outputs (some directly measured or estimated, some calculated as a function of other inputs and outputs with internal equations written by the user). Control inputs include physical variables adjusted manually, setpoints, and control logic parameters (such as gains for first-level controllers). Some important families of calculations are: (1) mass and energy balance equations to estimate certain results which may not be measured directly; (2) estimations of final results based on intermediate and input variables (e.g., NOx based on more readily measurable operating variables); (3) calculations of consistency vs. constraints or specifications, such as CPK and Loss Functions; and (4) economic equations taking all costs (and potential revenues) into account.

Multiple objectives: The evaluation of process performance is determined in quantitative terms defined by the team, where objectives are set by management. Individual objectives might relate to measures such as yields, production rates, economic evaluations (costs and revenues), quality, safety and equipment life, losses, emissions, byproducts, and satisfaction of regulatory constraints. Basically, if performance may be measured or estimated with sufficient accuracy and on a timely basis to learn from it, it may be taken into account. Goals are represented by: (a) a "Performance Index" or "objective function", an output to be maximized or minimized (which may be a directly measured value, or a function of other variables; (b) by necessary constraints on inputs and outputs.

Processes with noise: It deals effectively with process outputs that have "noise". Noise is the level of output data variations when inputs remain constant. Like all empirical solutions, the larger the noise the less effective it will be.

May use prior valid data: The analysis may be primed with valid data from previous runs.

Prior Model free: It does not require that the user provide mathematical/computer models of the behavior of the process. However, if the models are available it may use them to give the technology a jump-start. These models may just be approximations for some outputs as a function of some inputs.

Feed-forward adjustments: It may determine optimal adjustments for known values of uncontrolled inputs (e.g., resource allocation, materials characteristics, ambient conditions, process conditions). This is feed-forward optimization, based on predictive models (without requiring the process to deviate from objectives before corrective action takes place, such as in feedback control).

Feed-back adjustments: It may do feed-back optimization when the process changes slowly due to changes in unknown uncontrolled inputs.

Closed-loop implementation: It is applicable in the spectrum from Stand-Alone (no integration), to integrated but full hands-on human control (an Advisory capacity), to fully automatic on-line closed-loop optimization without requiring human intervention and interpretation (where ULTRAMAX provides reliable direct supervisory control, including efficient alerts).

Mathematical Formulation of SEO—The Process, Requirements and Optimum. The process behaves as follows (X, U, Y and are vectors):

$$Y = F(X, U) + \epsilon$$

where

X is the vector of adjusted inputs (control inputs), the decision that controls operational performance;

U is the vector of uncontrolled inputs, with values determined elsewhere (by people or nature);

Y the vector of outputs (after transients due to readjustments), the outcome or consequence from the inputs X,U.

Y0 is the value of the Performance Index or Objective Function;

F(X,U) is the steady-state mean (i.e., after transients due to readjustments) process output vector, or the "response". As we shall see, the form of F is unknown, the same as for $\epsilon$ below.

F, as representative of production processes, is relatively "smooth" in the area of interest. F may possibly be changing slowly with time (or equivalently, changing because of slow changes in unknown uncontrolled inputs not included in U).

$\epsilon$ is an bell-shaped noise vector with mean zero and covariance matrix $\Sigma$ with the diagonal of variances, whose square root is the standard deviation, sigma or noise vector N. It is most likely affected by X,U. With the understanding, contrary to remarks in vogue in the last few years in certain fields, that very few processes produce any data following a Normal distribution. Note that there are almost no physical principles that indicate that process outputs should be normally distributed (except, e.g., the energy emitted by a black object vs. the log of the frequency; the addition of several distributions of similar independent standard deviations—Central Limit Theorem). On the contrary, for instance, a process often places limits—resulting in trimming tails—which destroys a normal distribution. This has been confirmed by experience, where with sufficient data one almost always may prove that process output distributions are not normal.

$\epsilon$ is a property of the process AND of the OP, in particular, the inputs included and how Y is measured (e.g., averages of more raw data may have lower noise, especially if U does not change much). This concept of noise is smaller than in most other quality control analyses because changes in the known uncontrolled inputs do not contribute to noise, while they do in regular methods. Note that in this model "errors" are assigned only to the outputs. The inputs are presumed to be absolutely correct.

The requirements and optimal operations are defined as: Maximize the objective function (Performance Index) by selecting the adjustments X that satisfies the constraint requirements, given the value of U. The constraint requirements are:

(a) The mean process values almost never violates the upper (UC) and lower (LC) constraints. In this discussion, "mean" is used to express the average for the same values of the inputs; "average" is used for the average across time (with possible changes in inputs).

(b) The actual data for each run almost never violates a constraint by more than an amount "Minimum Important Difference" (MID). The MID allows for a "gray" area for the actual data constraint violation.

Mathematically: MaxX/U $\{F0(X,U)\}$—0 for objective function s.t. (wherein "s.t." means "subject to", or, within these constraint limits as a higher priority); that is, while satisfying these the constraint requirements:

Requirement (a):
$X_i \leq UC_i$=inputs with upper constraint UC;
$X_i \geq LC_i$=inputs with lower constraint LC;
$F_i(X,U) \leq UC_i$=outputs with upper constraint UC;
$F_i(X,U) \geq LC_i$=outputs with lower constraint LC.

Requirement (b):
$Y_i = F_i(X,U) + \epsilon_i \leq UC_i + MID_i$ (most of the time);
$Y_i = F_i(X,U) + \epsilon_i \geq LC_i - MID_i$ (most of the time).

The "most of the time" (b) requirement is translated into requiring that the practical worst noise level $\epsilon_i$ to be satisfied be 3-sigmas ($3*N_i$), called the 3-sigma Protection (although we are not using the criterion of the probability of violating constraints in order to avoid having to make assumptions about the distribution of the data):

$F_i(X,U) \leq UC_i - 3*N_i + MID_i$
$F_i(X,U) \geq LC_i + 3*N_i - MID_i$

Figure 2:
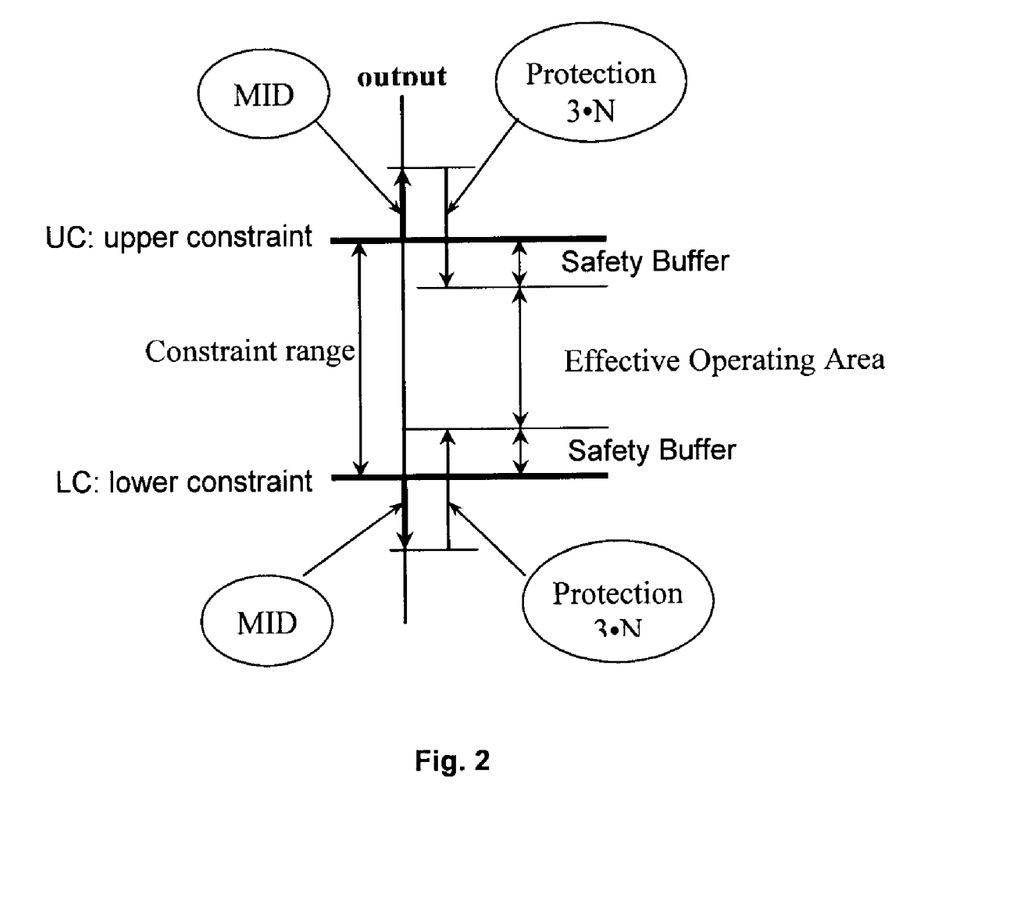
FIG. 2 is a diagram depicting an Effective Operating Area to satisfy an optimization requirement for the area of acceptable output means.

Similarly, practical optimization is when the achieved $F_0$ is within $MID_0$ of the optimal one defined above. See FIG. 2.

So, bringing both constraint requirements (a) and (b) into one composite set of equations, the optimum we are searching is defined as:

Given the values of U,
$Max_{X/U} \{F_0(X,U)\}$—0 for objective function;
s.t. $X_i \leq UC_i$—inputs with upper constraint UC;
$X_i \geq LC_i$—inputs with lower constraint LC;
$F_i(X,U) \leq UC_i - \max\{3*N_i - MID_i, 0\}$—outputs with upper constraint UC;
$Fi(X,U) \geq LC_i + \max\{3*N_i - MID_i, 0\}$—outputs with lower constraint LC which defines the optimum adjustment X* and the mean optimum outputs $Y^* = F(X^*,U)$; both for each value of U.

The practical objective is not quite to find the optimal X, but to define Xs that satisfy all constraints and produces mean outputs no further away from the optimal $F(X^*,U)$ than MID0. The set of such Xs defines the Window of Operations.

If there are upper and lower constraints and the Safety Buffer (defined below) is sufficiently large, there is no Operating Range and the process is totally incapable. In this case optimization makes little sense—the problem should be fixed.

An equivalent formulation of the output constraints is:
$UC_i - F_i(X,U) \geq \max\{3*N_i - MID_i, 0\}$—outputs with upper constraint UC;
$F_i(X,U) - LC_i \geq \max\{3*N_i - MID_i, 0\}$—outputs with lower constraint LC.

This form has a useful interpretation. The left-hand-terms are the mean Slacks (how far from constraints, negative is beyond); the right-hand-term is defined as the Safety Buffer; as follows:

Mean Slack$_i$=UC$-F_i(X,U)$—(upper);
Mean Slacks=$F_i(X,U)$-LC—(lower);
Safety Buffer$_i$=$\max\{3*N_i - MID_i, 0\}$ (recall, Protection=$3*N_i$);

Thus, the optimum output constraint requirements are simply that:

Mean Slack$\geq$Safety Buffer

Note that for the active outputs (that is, with active constraints) if the noise is $$N_i < \frac{MID_i}{3},$$

sufficiently small, then the Safety Buffer is zero, and the only constraint requirements is for the mean process values [requirement (a)]; and reduction of noise does not help except for the Performance Index. If the (mean output) constraints and the MIDs are properly defined from a business point of view, this is the sign of a process under good process control (and quality data).

On the other hand, if MID is zero, the only constraint requirement is for the actual process actual values [requirement (b)]. In this case, any reduction of noise for an active output results in potential improvements of the Objective Function (Performance Index).

Sequential Empirical Optimization (SEO). The characteristics of a Sequential Empirical Optimization solution to optimize a process are:

(1) It is Empirical: that is, series of run data $\{X,U,Y\}$ are known, but some (or all) F(X,U) and $\epsilon$ are not. In particular the structure of F is also not known except to assume reasonable "smoothness".

(2) It is Sequential: that is, it continually stores operating (run) data and continually uses the stored run data and extracts from it information and knowledge to create updated sequential advice to adjust the process next. Then a process run produces a new $\{X,U,Y\}$ which in turn is stored in the database and repeat the cycle. Thus SEO creates a series of $\{X,U,Y\}t$ stored in a data base. The first Xt is the adjustments at Baseline, defined by the user.

Note how the sequential analysis above emulates the process of a mind gaining experience through repeated action, and using the remembered actions, conditions and outcomes to make better action decisions in the future, and aspect or learning and skill development.

Sequential analysis has a very valuable advantage (à la [3] Wald): it uses the information in each sequential run immediately in order to refine knowledge and to decide where to run next. By comparison, in other more parallel empirical studies (DOE, Neural Networks) the value of the information is not used until the data is analyzed at the end. This is the most important reason why a properly implemented SEO technology is the fastest empirical optimizer available today. The other synergistic reason (bootstrapping) is that since SEO approaches the optimum faster, the database has relatively more data around the optimum, which is the most valuable data to understand the location of the optimum (recall, SEO does not assume knowing the structure of the process transfer function).

SEO Maximization is meant as a local optimum at the end-path of continuous improvements from the starting adjustments, and ideally jumping over minor local optima. In particular, finding "other mountains" to climb is taken as a responsibility of engineering or R&D, not of daily production.

The performance of a SEO solution—for the likely process forms of $Y=F(X,U)+\epsilon$ that will be optimized—is evaluated, basically, by:

How quickly the series $\{X,U,Y\}t$ converges to the optimum $\{X^*,U,Y^*\}$.

How closely the series $\{X,U,Y\}t$ approach to the optimum $\{X^*,U,Y^*\}$.

In manufacturing, which is a continual value generation situation, the performance of SEO is evaluated by the cumulative process performance while following the advice provided by the technology (The concept is very clear when there are no constraint violations: find the cumulative or average Performance Index. When there are violations, this approach requires placing a penalty for constraint violation, which is something somewhat arbitrary.)—or more specifically, since the implementation of optimization is started. (This clarification is made to take into account the performance losses and time that it takes to collect experimental data for model-based alternative approaches (such as DOE and NN); and the time to design and implement the first-principle models and collect data to validate it.)

In engineering and development the performance may be evaluated by the costs and delay incurred in the number of "experiments" and by how close the solution approaches the optimum.

Depending on the SEO technology used (or on how it is adjusted), achievements in terms of the objective function F0 may frequently be increased at the sacrifice of increasing the incidence of violating some constraints, and thus the SEO needs to proceed carefully. The sequence of Xt needs to be very "intelligent": low risk and effective. It must have a correct balance between:

(1) being conservative so as to avoid making the process violate constraints or sacrifice performance too much, (2) being bold, moving towards improved performance, (3) creating new data so that future models have improved prediction capabilities, (4) providing compensation for known values of the uncontrolled inputs (feed-forward optimization), and (5) reacting to changing behavior due to unknown uncontrolled inputs (feedback optimization).

The ULTRAMAX solution for SEO-Fundamentals. In addition to storing run data, the solution includes of two basic functions: Learning (creation of predictive models); and Synthesis (using the models to generate advice for the next run).

Learning, model building. Models of generic form $M(X,U) \cong F(X,U)$ are created for new values of U or when new run data is collected in the database, based on the set of historical run data $\{X,U,Y\}t$.

At the same time the technology creates:

(1) An Area of Confidence (AOC), which is the region in X,U where $M(X,U)$ is most accurate—within the region covered by $\{X,U\}t$.

It is calculated by an elaborate pattern application of the Mahalanobis [1936] distance which allows the AOC to be concave or composed of disjointed areas.

(2) An estimate $\Sigma$ of $\epsilon$ of and the noise n; The prediction models enable "What-if" estimation or outputs given the inputs (forward analysis).

Synthesis, Advice. Synthesis is almost the reverse of What-if. Synthesis is finding the values of the inputs which satisfy some criteria for the estimated outputs. Here it is "which-is-best" for decision-making. The solution is the same as for the theoretical definitions of optimum, except that:

(1) It is obtained with estimated functions M and noise N. In particular, the prediction error $E_i$ depends of the level of extrapolation, as typical of regression models.

(2) $\{X,U\}$ belonging to the AOC, where M is most accurate.

(3) Adds certain perturbations to that future models be more representative but without sacrificing performance much. (This is the leftover of the benefits of orthogonality in DOE.)

The Advice X for the next run is produced by:

MaxX/U $\{M0(X,U)\}$—0 for objective function;

s.t. $X_i \leq UC_i$—inputs with upper constraint UC;

$X_i \geq LC_i$—inputs with lower constraint LC;

$F_i(X,U) \leq UC_i - \max\{3*E_i - MIDi, 0\}$—outputs with upper constraint UC;

$F_i(X,U) \geq LC_i + \max\{3*E_i - MIDi, 0\}$—outputs with lower constraint LC;

$\{X,U\} \in$ AOC—Area of Confidence plus adding periodic perturbations Including the constraint of being in the Area of Confidence, in addition of assuring acceptable prediction errors, enables dealing with input data which follows certain patterns, such as near-collinearities. Note: For people accustomed to desiring orthogonal data, let us clarify that a properly formulated Optimization Plan will have independent control inputs, thus any collinearities are not the result of cause-and-effect relationships between the inputs. Note further that in moving the adjustments from the current region to the optimal ones, it is desirable to move along ridges so as achieve maximum cumulative performance. This leads to having near collinear inputs, but only due to an intelligent optimizer getting desired outcomes.

Note these two properties about M for SEO which yield significant simplification and effectiveness in calculations:

(1) It is not required to understand the effects of each input separately; it is just necessary to be able to predict results in the AOC region. Thus, with the protection afforded by the AOC, confounding of input effects is of little consequence.

(2) Trying to make M accurate away from the optimum (e.g., by making its generic form too involved or by fitting data in that region) is not only is irrelevant but it distorts the fitted models resulting in lesser accuracy around the optimum.

These properties are less demanding on $M(X,U)$ than the usual requirements for DOE, Neural Networks and First Principle models (each for different reasons).

Note this characteristic of SEO: if a sequential advice is relatively poor because of making an incorrect inference, the run is likely to provide data that reveals the issue: (good) sequential empirical decision analyses are self-healing.

Details—Learning (update models). The ULTRAMAX solution creates prediction models M in three ways. The solutions 1 and 2 are a multivariable quadratic or second-order Taylor approximation of the response surface F for each output as a function of all inputs.

(1) Bayesian Statistics. Models are crated with Bayesian statistics when there is little data. This compares with the computationally much faster Classical or Fisherian statistical models least-sum-square fits. Also, in general the Bayesian framework is superior for decision making analysis—as compared to scientific true-false assessments best made with classical statistics. Bayesian solutions enable us to utilize the information available in as little as two runs, with different input values, to already be able to move sequentially in a direction of likely improvements.

This thought problem illustrates what is desirable. Imagine: (1) A process with two adjustments and one result to be maximized; (2) The two adjustments are represented by two sides of a room, and the results by height; (3) Two process runs (with different adjustments and different results), which correspond to two points in space in the room (while explaining this, hold the point at the tips of the thumb and index finger of each hand).

Now, ask the question: in which direction should we change the adjustments next with the highest likelihood of improving results? Obviously we would move the adjustments from the low performing run to and passing the high performing run. (1) The simplest prediction model structure that would recognize the effects of the adjustment inputs is a linear model with three parameters (a constant and a coefficient for each input). (2) Classical statistics may not create a prediction model with the above data (there are two data points to estimate three parameters). (3) Bayesian statistics may create such a model; and the result matches what our intuition indicates: move adjustments from the lower height run towards the higher height run, going beyond the higher run adjustments. (The MID indicates how much further we may go.) (4) The above holds true for any number of inputs! Thus, if we have 20 adjustments, ULTRAMAX's sequential Bayesian models will likely be obtaining performance improvements starting from the third run, while classical statistics maynot even venture a guess until the 22nd run. Neural Networks, having many more coefficients, would be much worse in this respect.

The application of Bayesian regression starts with linear models with very limited data, and then moves on with the full quadratic with more data. The solution is explained by Moreno (2006) and Hurwitz (1993):

Adelman, A., and W. F. Stevens (1972). "Process Improvement by the 'Complex' Method," AIChE Journal, Vol. 18, No. 1, p. 20.

Bhateja, C. P. and C. W. Moreno, (1989) "Practical Optimization of Production Grinding Systems", SME Modem Grinding Technology Clinic, Oct. 10, 12, 1989; Detroit, Mich.

Box, M. J. (1965). "A New Method of Constrained Optimization and a Comparison With Other Methods," Computer Journal, Vol. 6, p. 42.

Box, G. E. P., and N. R. Draper (1987). Empirical Model Building and Response Surfaces, John Wiley & Sons, New York, N.Y.

Box, G. E. P., and N. R. Draper (1969). Evolutionary Operations, John Wiley & Sons, New York, N.Y.

Colosimo, B. M., del Castillo, E. (2006). "Bayesian Process Monitoring, Control and Optimization" Chapman & Hall/CRC. ©2007; Boca Raton, Fla., USA. December 2006. See C. W. Moreno (2006) below.

Draper, N., and H. Smith (1966). Applied Regression Analysis, John Wiley & Sons, New York, N.Y.

Dharmarajan, N. N., and Patterson, P. D. "Boiler Tuning with SPO: Critical First Step in NOx Compliance Strategy of Central & South West Corporation." Paper presented at AWMA Conference and Expo, Nashville, Tenn., June 1996.

McVay, M. and Patterson, P. D. (1998) "Illinois Power's On-Line Dynamic Optimization of Cyclone Boilers for Efficiency and Emissions Improvement", Int'l Joint Power Generation Conference, Baltimore, Md., Aug. 24, 1998.

Moreno, C. W. (1993) "How Modem 'Smarter Not Harder' Technologies may Simultaneously Maximize the Combination of Pollution Reduction and Business Success", Conference on Environmental Commerce, CONEC'93, Chattanooga, Tenn., Oct. 17-20, 1993.

Moreno, C. W. (1994) "Gaining Control of Plastic Forming Machines with new Technology for On-line Adjustments", Structural Plastics Conference, Apr. 10-13, 1994, Washington, D.C.

Moreno, C. W. (1995-2006) The Blue Book: Maximizing Profits through Production, Ultramax Corporation, Cincinnati, Ohio, USA.

Moreno, C. W. (1999) "Improvements Through Process Adjustments", Amerimay Statistical Association Quality and Productivity Research Conference, May 19-21 1999, Schenectady, N.Y., USA.

Moreno, C. W. (2001) "Comparison of two well known Methods for Optimizing Power Plant Operations", 44th Annual ISA Power Industry Div. Conference, Orlando, Fla., USA Jul. 7-13, 2001

Moreno, C. W. (2006) "Software: A gentler step-up", InTech, ISA (Instrumentation, Systems and Automation) Society, April 2006, pp. 45. www.isa.org/InTechTemplate.cfm-?Section—Article_Index1&template=/ContentManagement/ContentDisplay.cfm&ContentID=53257

Moreno, C. W. (2006) "An Application of Bayesian Statistics to Sequential Empirical Optimization" Chap. 11, page 291, of "Bayesian Process Monitoring, Control and Optimization" by Colosimo and del Castillo—see above.

Moreno, C. W. and Yunker, S. B. (1993), "Reducing NOx Emissions and Improving Boiler Efficiency Using Synthetic Intelligence", Conference on Expert System Applications for the Electric Power Industry, Phoenix, Ariz., Dec. 8-10, 1993.

Nachtsheim, C. J. (1987). "Tools for Computer-Aided Design of Experiments", Journal of Quality Technology, Vol. 19, No. 3, July 1987, pp. 132-160.

Sachs, E. M., R. Guo, S. Ha, and A. Hu, (1991), "Process Control System for $VLS_1$ Fabrication", IEEE Transactions on Semiconductor Manufacturing, Vol. 4, No. 2, May 1991 Abstract Spendley, W., G. R. Hext, F. R. Himsworth (1962). "Sequential Applications of SIMPLEX Designs in Optimization and EVOP," Technometrics, Vol. 4, pp. 441-61.

Wald, A. (1947). Sequential Analysis, John Wiley & Sons, New York, N.Y.

Walters, F. H. et al. (1991). Sequential SIMPLEX Optimization, CRS Press, Inc., Boca Raton, Fla.

True Bayesian analysis, involving multidimensional integrals, are very time consuming—as compared to classical regression analysis. Quasi-Bayesian regression models are created with this computational short-cut: use dummy "prior data" with "null" knowledge and classical regression analysis. The result is very similar to ridge regression, which was illustrated by Hurwitz to be equivalent to the Bayesian analysis.

When there is sufficient data to calculate all coefficients with Classical statistics and have enough extra to calculate the noise with classical regression, the models are said to be "complete".

Full quadratic models have $$\frac{(N+1)(N+2)}{2}$$

coefficients, where N is the number of inputs. The minimum number of run data required to get complete models is this value plus the desired number of degrees of freedom, approximately 2*N+. Then PRIOR=0 in the Model and the Coefficients reports, and models are "complete". Then also most indicators of model suitability such as the "noise" and "signal" became more reliable.

Goal-oriented, Locally Accurate Models. A breakthrough awareness and principle is to realize that: For optimizing, we only need to predict well around the optimum (or best predicted running conditions). (There are a few more requirements. The important thing is to recognize that predicting equally well everywhere is not very relevant for optimization, ans is the burden of virtually all empirical solutions.)

(1) When more data than necessary for complete models becomes available, weighted linear regression is used to focus on optimal operations, to include only data which produces the most accurate models around where the best estimated results. (Obviously, this is not regular regression.) Note that for doing optimization, representing the response surface away from the optimum is actually a detriment since this tends to distort the fit of the models around the optimum (unless the model structure is very representative).

(2) Locally accurate quadratic models largely eliminate the concern of lack-of-model fit for "smooth" response surfaces.

(3) The models also weight older data less when it detects deviations in process behavior from past patterns. (This happens when the process is deigned "dynamic".)

(4) The input spread of the series $\{X,U,Y\}_t$ depends on the noise and the MID.

Calculated outputs. Calculated outputs are a function of inputs and/or of other predicted outputs. These models have the following characteristics:

(1) they provide guidance as to which direction to follow for improvements even with limited data.

(2) they adapt well to slow dynamic changes in process behavior due to unknown causes;

(3) they tend not to be badly fooled into fitting noise rather than the underlying process behavior (due to the Bayesian analysis with little data, and due to heuristics to select data when there is excess data to generate locally accurate models).

(4) since they have relatively few coefficients (e.g., as compared with Neural Networks), they are capable to extrapolate further going from the starting set of adjustments to the optimal ones.

(5) deal effectively with smooth response surfaces with structural non-linearities and smooth non-constant interactions among the inputs (e.g., curved ridges).

Synthesis (generate advice). The SEO resolution of the mathematical formulation above is done with a non-linear programming algorithm which may:

(a) solve conditional optimization;

(b) has reasonable abilities with mixed-integer solutions (but not when approaching few categorical values such as zero-one programming).

Synthesis is created by this prioritization:

$1^{st}$ inputs obey their constraints.

$2^{nd}$: when giving Advice only (not for the Optimum Estimate), give Advice where each input does not change by more than its MID. (There is also a multivariable limit on the "travel" of the re-adjustments: Travel$\leq$PAR(41).)

$3^{rd}$: $\{X,U\} \in AOC$, to assure relative certainty of estimates;

$4^{th}$: Multivariable limit on the "travel" of the re-adjustments: Travel (A Mahanobis distance.)$\leq$PAR(41);

$5^{th}$: outputs obey their constraints;

$6^{th}$: optimize the Performance Index or objective function (often plus a perturbation function).

Synthesis may be seen as the coding of "volition", or a goal oriented attitude in the part of the technology, to attempt desired better results not experienced before. A basic reason this is possible is because of the implicit assumption of the reasonableness of interpolation and extrapolation in systems with gradual variables. With the current technology this is much more difficult to achieve with categorical (extremely discrete) decision problems. Other specifics about the technology used were published in Moreno & Yunker 1992, 1993, Moreno 1986, 1988, 2006, as listed above.

Reference to Artificial Intelligence. All together, Learning and Synthesis, like most algorithms, are a series of heuristics or rules which are based on the accumulated experience of experts and the creators of the technology. As such, the technology may be seen as an "Expert System" to learn how to adjust a process to optimize its performance.

I have previously noted the distinction that ULTRAMAX has a domain of a relatively small number of variables with infinite values, while traditional Expert Systems tend to deal with very many elements, each of which is characterized by a few discrete (categorical) values. Further, it suggests that "Artificial Intelligence" should have the characteristics of Cognition and Volition, where Cognition is defined as "Learning about how a system is and may be", and Volition as "Creating or selecting options based on an evaluation of consequences". Reflex behavior, such as a standard PID control unit for production environments, has neither cognition nor volition, and therefore it is not Artificial Intelligence.

Some further characteristics:

Types of variables: It is restricted to using control inputs and outputs which behave gradually, in order to be able to use the modeling methods described above. "Gradual" means that the variables are potentially continuous, but may be discretized in small steps. It does not handle categorical factors except for the component inputs.

Time frame: ULTRAMAX runs "real-time" with a time frame for process adjustments in the order of every several minutes to hours, or batch time. While software CPU is a consideration for short cycles, the most frequent determining factors of the time between adjustments (Run Time) are: (a) in continuous processes: how long it takes to get to steady-state due to readjustments of the control inputs, so that the output data truly reflect the current inputs, rather than effects from previous ones (unless using the "Transient Version" of SEO); (b) in batch processes: the length of a batch processing; (c) during the first cycles while converging the optimum, how long it takes after the completion of a run to measure the values of Y—e.g. from a laboratory example. (d) how frequently U changes. By comparison, the time frame for (first-level) "process control" is in the order of a second or fractions.

In process control this is what most people understand as "real-time". (a) Quick adaptation to alternate goals: The evaluation of process performance may be made through calculated variables (most frequently the Performance Index is calculated), which may be a function of Global Factors. The Global Factors represent targets, tolerances, unit costs, etc., and they may easily be changed from a central location in the software. In particular, calculated variables are recalculated with new factors to portray old (valid) physical data with today's objectives and evaluation factors, and the sequence of advice will move quickly to the new optimal conditions. This also means that the Optimization Plan does not have to be worked through in total detail. In fact, it is common for the awareness of true optimization objectives to evolve significantly during the course of SEO.

Noise: Changes in known uncontrolled inputs are not a source of "noise", as in most other statistical approaches. For ULTRAMAX their effects are understood, and managed. While uncontrolled inputs are "special causes" for SPC, ULTRAMAX provides the means to cope with them. The unknown uncontrolled inputs, and changes in the known uncontrolled inputs within a run are noise factors.

Optimum Estimates: There are three "flavors" of Optimum Estimates made by the software:

(1) The Potential or Projected Optimum Estimate (POE) (within the AOC), where the expected prediction errors are calculated on the presumption that there is plenty of data around it as if it were interpolation, as when there is actual data around this optimum.

(2) The Advice & Optimum Estimate (AOE) has sufficient protection to be an advice to actually run the process. Here the expected prediction errors take into account the increase in uncertainty due to extrapolation into regions with less or no data. (For the AOE, when extrapolating, the protection sometimes needs to be less than 3-sigma in order to enable faster progress moving towards an optimum close to output constraints.) When AOE is close to POE, then ULTRAMAX has converged to the optimum—which happens when the SDF of Opt.Est.≦0.4 regularly.

Advice: (1) The Travel-Limited Path (TLP) are intermediate advice moving from the current adjustments towards the AOE, but which maynot move directly to the AOE because of constraints on of maximum changes in adjustments. (Defined by the user through PAR(59) and the MID.) (2) Advice w/ Exploration, the product of the perturbation.

Performance Characteristics. Starting from the current operations, ULTRAMAX's Sequential Optimization provides higher cumulative process performance—cumulative contribution to profits or any metric defined by the end-user—than any other empirical technology today, and perhaps than ANY technology—The alternate to "empirical" is "first-principle based" models, which take a very long time to make and validate to the same degree of accuracy—while the process continues working at the current conditions. One case where first-principle models may do better is when required measurements are not available on-line. This is equivalent to taking fewer runs (readjustments) to approach the optimum, and to get closer to the optimum.

This property is valid when starting away from a (local) optimum (If starting at an optimum, the best performance is obtained by doing nothing different, which is a strategy which does not allow getting improvements when starting away from the optimum.); and applies: (a) Almost definitely when there is only one local (and thus global) optimal operating performance. (b) Almost always when the process is dynamic (slow changes in unknown uncontrolled inputs), as alternate technologies today tend to be much more static. (Still, ULTRAMAX may only handle slow changes in unknown uncontrolled inputs.) (c) Most probably for a year or longer, when there are multiple local optima and ULTRAMAX converges to an inferior local optimum.

ULTRAMAX may converge to a local optimum because it starts from current operating conditions and follows a maximum-gain path towards the top of a "mountain of performance", which may be a local optimum. (Considerable more effective than gradient-ascent, especially when there are interactions between the inputs.)

By comparison, Neural Networks (NN) [like Design of Experiments (DOE)] require up-front many experimental runs with the production process itself, aiming at covering a large area of potential running conditions. Note that during these experiments the cumulative performance suffers significantly (constraint violations, unit costs, throughput, quality, emissions, equipment life, etc.)—which constitutes a significant hidden cost of the implementation.

However, in the case of NN, the model may represent various "mountains of performance" within the explored input area, and the attached optimization logic would be able to select the best such mountain. This best mountain may be better than the one that ULTRAMAX converges to. In such case, in the course of time and as long as the process is not changed or improved, the NN cumulative performance will eventually exceed that obtained with ULTRAMAX. If the process changes then the NN models will have to be recreated with a new set of experimental runs, incurring again the associated operating costs; while ULTRAMAX, with a lag, automatically keeps up with it.

Note the contrast: SEO is both an interpolation and a sequential extrapolation tool, while Neural Networks and Design of Experiments are basically interpolation tools. Note also that no interpolation technology may assure identifying the global optimum, as it might exists outside the area chosen up front for gathering the experimental data, and will remain so until the experimental area is expanded to where the global optimum is. On the other hand, if there is only one local optimum, ULTRAMAX will converge towards it wherever it is; and will maximize the cumulative performance. (More narrowly, ULTRAMAX will always converge so some optimum, while NN and DOE only to one within the area of data coverage.)

Technical Performance. The performance capability of ULTRAMAX is, in general and simplified terms, as obtained through replicated experiments optimizing a variety of simulated processes:Regularly, ULTRAMAX's SEO average performance will get relatively quickly as close to the optimum as the order of magnitude of the noise level.

The losses vs. ideal Performance Index in the Effective Operating Area (in turn reduced by the noise in the outputs) increase with the number of inputs of the application; and is relatively better the more active outputs are calculated. (To the extreme that if all outputs are calculated then no data is necessary—the reality is fully represented by calculations.) Further conditions are described below.

Recall that for ULTRAMAX, noise DOES NOT INCLUDE the effects of changes in uncontrolled inputs for which there is data from run to run, while noise does with many quality control solutions.

This assumes not running into a region of "insensitivity" (defined below).

As a practical consequence of the above:

Let us assume that at the starting operating conditions constraints are regularly satisfied, namely, gains are only on the Performance index or objective function. To get improvement the noise of the objective function $N_O$ needs to be small (like $\frac{1}{3}^{rd}$) in comparison to the potential improvements in going to the optimum. If the potential improvements are lower than the noise then we will only be able to prove that we are running at near-optimal conditions for the current noise level.

It is possible to get better optima by reducing the noise of the objective function and active constraints, which is practical to do until $3*N=3*sigmas \leqq MID$. The condition $3*N=3*sigmas \leqq MID$:

makes sense because such level of control on operations would regularly satisfy management daily concerns from production about forecast and safety (as represented by MID values management defined). (This has been an underlying message in Quality Control, such as Dr. Deming, Dr. Juran, Six-Sigma, etc.) This is a lesser requirement than Six-Sigma, with the consequence that where Six-Sigma is already implemented the data will have even less noise and this will make it very easy to optimize well.

Note that the variables used, MIDs, objectives and constraints may change with time as the business conditions and awareness of issues change (easily done with an sequential analysis solution).

ULTRAMAX is a tool for active on-going process management, not to be placed in the background to run-by-itself and be virtually ignored, otherwise the optimization plan will sooner or later become obsolete; and further, the end-user will miss the advantages detecting problems (out of statistical control condition), and will miss developing a better understanding of the process.

Why better? ULTRAMAX's SEO is faster for two basic reasons:

(1) Most importantly, because of the Sequential Analysis; the fact that the information in new data is used right away to generate knowledge, rather than leave the information unused in model-centric solutions until the data is analyzed at the end.

(2) Bayesian statistics, that enable moving into possible improvements starting with the third run.

ULTRAMAX's SEO is likely to get closer to the ideal optimum because it uses locally accurate models.

Other Specifics. The run averages deviate from the optimum $F_0(X^*,U)$ due to:

(1) Imperfect knowledge because of the existing noise N in the data, and lack of model fit. In static processes these effects decrease as more data becomes available. The amount of sequential data converging to the optimum has two positive effects:

(1) increases precision by the traditional $1/\sqrt{n}$ factor, and (2) enables the local model to be accurate in the smaller region where the lack of model fit (or variations in the noise level) is not important in comparison to the existing noise.

(2) Failing the (B) condition below if gradients get reduced too much in the path converging to the optimum.

(3) The need to maintain a spread of the input data so that the continually updated empirical models maintain the knowledge about F(X,U) around the optimum, and also to pick up slow dynamic changes from unknown causes. (The mechanism to pick up slow changes of unknown origin is to treat the process as dynamic (PAR(49)=1), which enables the data weighing to discount data because of its age. ULTRAMAX will gradually realize that using later data creates better fits, and this provides for gradual and slow feedback adjustment of the new modes of operations (not unlike the concept of running average). Conceptually, continuously changing unknown uncontrolled inputs may change at such frequencies that ULTRAMAX might enter a situation of resonance; but this has never been seen.) The amount of spread may be managed.

The above performance characteristics apply when:

(A) All the ULTRAMAX Parameters are set at default, or with some refinements suggested by Ultramax Corporation.

(B) Do not run into an insensitivity condition.

Common sense (and theory) indicates that convergence to an optimum will not happen if the noise is too large in comparison to the gradient (More explicitly, this is the "effective" gradient, the change in output for the likely changes in inputs, not the infinitesimal gradient of calculus. It may be said that we are concerned with "difference analysis" rather than "differential analysis", as it befits making sequential adjustments with significant changes in values. Thus, in addition to the requirement of the slope of a ridge, we are concerned with the curvature of a ridge.) times the willingness to change the inputs. (The same reason why Screening Experiments sometimes fail.)

Limits to changes in the control inputs from one set of adjustments to the next is determined by their MID and constraint ranges on inputs; and if small enough it will hung up Sequential Optimization. A metric that reflects this situation is a small Signal—but amazingly, ULTRAMAX has optimized with small signals also.

Figure 3:
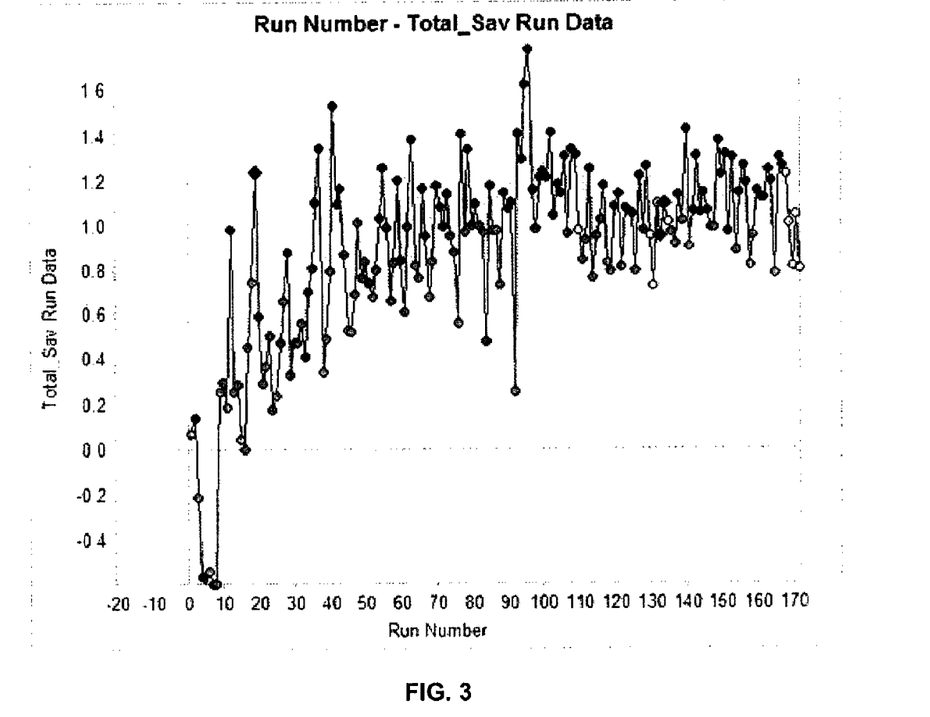
FIG. 3 is a plot of results from the Individual System Performance Management apparatus.
Figure 4:
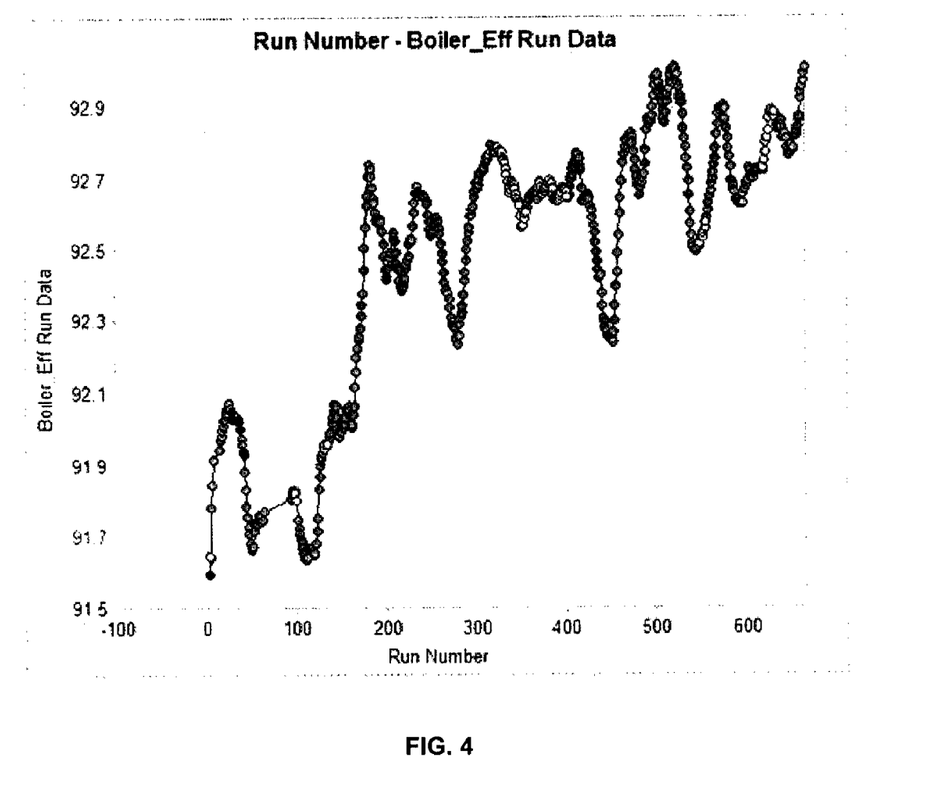
FIG. 4 is another plot of results from the Individual System Performance Management apparatus.

Examples of outputs from the ISPM apparatus are depicted in FIGS. 3 and 4.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

What is claimed is:

1. An individual system performance management device said device adapted to provide adjustment advice for continual near-best operating performance of said system; said device incorporating algorithmic analysis/synthesis within the device such that said device refines its learning about said system's response as operating data is collected; said device further providing updated adjustment management advice; said device being further adapted to detect abnormal behavior for expert analysis and resolution and to provide dynamic awareness for when there are changing conditions; and wherein the device is adapted to perform both forward analysis and backward analysis, where forward analysis is based on an estimated input and backward analysis is based on an estimated output.

2. The device of claim 1 where said algorithmic analysis/synthesis is accomplished by Sequential Empirical Optimization.

3. The device of claim 1 where said system is a management system for a patient with a chronic disease adapted to provide disease management advice under usual states for that disease, said advice being focused on what said patient should or could do and being tailored to the specific conditions and response of the patient.

4. The device of claim 3 wherein said chronic disease is diabetes.

5. The device of claim 1 wherein said analysis is accomplished locally.

6. The device of claim 1 wherein said analysis is accomplished by a centrally-located server.

7. The device of claim 3 wherein said device generates suggested treatment based upon individual response.

8. The device of claim 3 wherein patient data is collected by one or more medical sensor devices.

9. The device of claim 3 wherein when said device detects abnormalities and directs said patient to obtain further advice and diagnosis by medical experts.

10. The device of claim 3 wherein the determination of treatment is determined by recording and analyzing said patient's response to conditions.

11. The device of claim 3 wherein said device is dynamic in that it is adapted to consider changes in individual response as a function of time.

* * * * *